US006955851B2

(12) United States Patent
Hanson et al.

(10) Patent No.: US 6,955,851 B2
(45) Date of Patent: Oct. 18, 2005

(54) HYDROXYARYL PHOSPHINE OXIDES, GLYCIDYL ETHERS AND EPOXY COMPOSITIONS, COMPOSITES AND LAMINATES DERIVED THEREFROM

(75) Inventors: Mark V. Hanson, West Lafayette, IN (US); Larry D. Timberlake, West Lafayette, IN (US)

(73) Assignee: PABU Services, Inc., Wilmington, DE (US)

( * ) Notice: Subject to any disclaimer, the term of this patent is extended or adjusted under 35 U.S.C. 154(b) by 69 days.

(21) Appl. No.: 10/732,018

(22) Filed: Dec. 10, 2003

(65) Prior Publication Data

US 2004/0121990 A1 Jun. 24, 2004

Related U.S. Application Data

(62) Division of application No. 10/077,701, filed on Feb. 14, 2002, now Pat. No. 6,733,698.
(60) Provisional application No. 60/268,975, filed on Feb. 15, 2001.

(51) Int. Cl.$^7$ ......................... B32B 27/04; C08G 59/06; C08G 59/14; C08L 63/00
(52) U.S. Cl. .................... 428/297.4; 428/607; 525/480; 525/507; 525/523; 525/525; 528/99
(58) Field of Search ...................... 252/609; 428/297.4, 428/607; 525/523, 480, 507, 525; 528/398, 99; 549/219; 568/17

(56) References Cited

U.S. PATENT DOCUMENTS

| | | | |
|---|---|---|---|
| 3,676,393 A | 7/1972 | Piirma ..................... 260/45.7 P |
| 3,751,481 A | 8/1973 | Weinberg ............. 260/601.5 P |
| 3,784,638 A | 1/1974 | Lambert .................. 260/526 S |
| 3,852,362 A | 12/1974 | Lambert ............... 260/606.5 P |
| 4,126,602 A | 11/1978 | Salee ........................ 260/40 R |
| 4,187,259 A | 2/1980 | Salee .......................... 525/219 |
| 4,211,687 A | 7/1980 | Salee ........................ 260/40 R |
| 4,221,694 A | 9/1980 | Salee ........................ 260/40 R |
| 4,251,429 A | 2/1981 | Salee ........................ 260/40 R |
| 4,256,625 A | 3/1981 | Dachs ...................... 260/40 R |
| 4,284,549 A | 8/1981 | Salee ........................ 260/40 R |
| 4,345,059 A | 8/1982 | Fretz, Jr. et al. ............ 528/102 |
| 4,444,960 A | 4/1984 | Salee et al. ................. 525/534 |
| 4,866,155 A | 9/1989 | Mueller et al. ............. 528/191 |
| 4,973,631 A | 11/1990 | McGrath et al. ............ 525/534 |
| 5,376,453 A | 12/1994 | von Gentzkow et al. ... 428/415 |
| 5,399,654 A | 3/1995 | Ko et al. ...................... 528/99 |
| 5,458,978 A | 10/1995 | Bottcher et al. ............ 428/413 |
| 5,508,462 A | 4/1996 | Bright et al. ................. 558/99 |
| 5,576,357 A | 11/1996 | Bayer et al. ................. 522/170 |
| 5,587,243 A | 12/1996 | von Gentzkow et al. ... 428/413 |
| 5,648,171 A | 7/1997 | von Gentzkow et al. ... 428/413 |
| 6,097,100 A | 8/2000 | Eguchi et al. ............... 257/787 |
| 6,177,489 B1 | 1/2001 | Okuse et al. ................ 523/451 |
| 6,403,220 B1 | 6/2002 | Brennan et al. ............ 428/413 |

FOREIGN PATENT DOCUMENTS

| | | | |
|---|---|---|---|
| DE | 2254 902 | 5/1973 | ............. C07F/9/50 |
| DE | 3510416 A1 | 9/1986 | ............. C07F/9/53 |
| EP | 0 412 425 B1 | 8/1990 | .......... C08G/59/40 |
| EP | 0 795 570 A1 | 9/1997 | .......... C08G/59/40 |
| EP | 1 116 774 A2 | 7/2001 | .......... C09K/21/14 |
| JP | 61-134395 | 6/1986 | ............. C07F/9/50 |
| JP | 5-57991 | 8/1993 | ............. C07F/9/53 |
| JP | 10-364988 | 7/2000 | ........... B32B/27/18 |
| JP | 2000-186186 A | 7/2000 | ............. C08L/63/00 |
| RU | 620491 A | 7/1978 | ............. C07F/9/53 |
| WO | WO 99/00451 | 1/1999 | ......... C08K/5/5333 |
| WO | WO 01/42253 | 6/2001 | ............. C07F/9/53 |
| WO | WO 01/42359 | 6/2001 | ........... C08L/63/00 |

OTHER PUBLICATIONS

"Ir Spectra of the Oxides and Sulphides of Triarylphosphines and Triarylarsines", V. Baliah et al., J. Indian Chem. Soc., vol. 67, May 1990, pp. 430–431.

"Synthesis and Solid–State Structures of Substituted Arylphosphine Oxides", Craig M. Whitaker et al., J. Org. Chem. 1995, 60, 3499–3508.

"Derivatives of Triphenylphosphine and Triphenylphosphine Oxide", Allen E. Senear et al., J. Org. Chem. 1960, 25(10), pp. 2001–2006.

"Synthesis and Characterization of Epoxy–Novalac Composite–Steel Adhesives", M.B. Bump et al., Polymer Materials Science & Engineering, V83, 2000, pp. 19–20.

"The Mass Spectra of Some para Substituted Triarylphosphines and Triarylphoshpine Oxides", G. Marshall, Organic Mass Spectrometry, vol. 16, No. 6, 1981, pp. 272–274.

"N–Phenyl–P,P,P–triarylphospha–?5–azenes, Triaarylphosphines, and Triarylphosphine Oxides. Substituent Effects on 15N, 31P, and 13C NMR Spectra", of W–N Chou et al., J. Org. Chem. 1991, 56, pp. 2762–2769.

"Synthesis and Characterization of Phosphine Oxide Diol Modified Epoxy Adhesives", M.A. Hickner et al., Polymer Preprints 2000, 412), pp. 1372–1373.

"Synthesis and Flammability of Copoly(isophthalamide)s. II. With Pendant Phosphorus Groups", K.G. Gravalos, Journal Polymer Science: Part A: Polymer Chemistry, vol. 31, 1993, pp. 1355–1364.

(Continued)

*Primary Examiner*—Robert Sellers
(74) *Attorney, Agent, or Firm*—Baker & Daniels LLP (57) ABSTRACT

The invention provides new compositions of matter that are capable of forming cross-linked polymeric materials upon reaction with various known epoxy-containing compositions. Thus, the compositions of this invention are useful in the manufacturing of prepregs and laminates for PWB applications among many other uses. Preferred compositions of this invention include substituted hydroxyarylphosphine oxide mixtures, the glycidyl ether derivatives, or the epoxy resin oligomer adducts derived therefrom. The materials provide for laminates that have higher glass transition temperatures, improved thermal stability, and that are free of halogen.

10 Claims, 1 Drawing Sheet

OTHER PUBLICATIONS

"NMR Spectral Data: A Compilation of Aromatic Proton Chemical Shifts in Mono– and Di–Substituted Benzenes", B.L. Shapiro et al., J. Phys. Chem. Ref. Data, vol. 6, No. 3, 1977, pp. 919–991.

"Sn–Zn System Lead Free Solder Paste", Japan Printed Circuit Association, Apr. 2001, pp. 1–18.

"Phosphorus–Containing Epoxy for Flame Retardant. I. Synthesis, Thermal, and Flame–Retardant Properties", Y–L Liu et al., Journal of Applied Polymer Science, vol. 61, 1996, pp. 613–621.

"Intumescent Fire Retardant Epoxy Resins", G. Camino, Chemistry and Technology of Polymer Additives, Chapter 7, 1999, pp. 108–134.

Chemical Modification of Epoxy Resins by Dialkyl (or Aryl) Phosphates: Evaluation of Fire Behavior andl., Journal of Applied Polymer Science, vol. 62, 1996, pp. 1855–1868.

"Syntheses, Structure, Reactivity, and Thermal Properties of New Cyclic Phosphine Oxide Epoxy Resins Cured by Diamines", M–D Shau et al., Journal of Polymer Science: Part A: Polymer Chemistry, vol. 34, 1996, pp. 387–396.

"Structure Characterization, Reactivity, and Thermal Properties of New Cyclic Phosphine Oxide Epoxy Resin Containing Tetra–Oxirane Rings", M–D Shau et al., Journal of Applied Polymer Science, vol. 68, 1998, pp. 1397–1409.

"Synthesis, Characterization, and Polymerization Reactions of Abx Triarylphospine Oxide Monomers", E. Fossum, Polymer Preprints 2000, 41(1), pp. 200–201.

"Self–extinguishing Epoxy Resins without Flame Retardants: Their Potential Use in Electronics", Y. Kiuchi et al., The 12th Annual BCC Conference on Flame Retardancy, Recent Advances in Flame Retardancy of Polymeric Materials, May 21–23, 2001.

"Synthesis, Characterization, Thermal, and Flame Retardant Properties of Phosphate–Based Epoxy Resins", Y–L Liu et al., John Wiley & Sons, Inc., 1997, pp. 565–574.

"Copper–Clad Laminates for Use as Printed Circuit Boards", M. Perry et al., Plastics and Resin Compositions, Royal Society of Chemistry, 1995, pp. 74–99.

"Nucleophotic Constants of Diphenyl P", Teoreticheskeye I eksperimental'naya Khimiia, v. 3(6), 1967, pp. 824–829.

HYDROXYARYL PHOSPHINE OXIDES, GLYCIDYL ETHERS AND EPOXY COMPOSITIONS, COMPOSITES AND LAMINATES DERIVED THEREFROM

CLAIM FOR PRIORITY

This application is a divisional patent application of U.S. patent application Ser. No. 10/077,701 filed Feb. 14, 2002, now U.S. Pat. No. 6,733,698, which application claims the benefit of he filing date of U.S. Provisional Patent Application Ser. No. 60/268,975, filed Feb. 15, 2001. The priorities of the foregoing applications are hereby claimed.

FIELD OF THE INVENTION

This invention relates to new compositions of matter, such as hydroxyarylphosphine oxide mixtures and derivatives thereof, which are useful as flame retardants for epoxy resin compositions, as well as a process to prepare these mixtures. More particularly, though not exclusively, this invention relates to novel compositions of hydroxyaryl and/or glycidoxyarylphosphine oxides, mixtures thereof, and epoxy oligomers and compositions derived therefrom, useful for forming a variety of curable compositions. The present invention is also directed to flame retardant epoxy resins used to prepare prepregs, laminates, particularly copper clad laminates useful in manufacturing electronic components such as printed wiring boards without the use of halogen-containing compounds.

BACKGROUND OF THE INVENTION

Composite materials based on epoxy resins have been used in a variety of day-to-day applications for a long time and continue to have considerable importance because of their versatility. A specific example of such an application includes but is not limited to electrical laminates used in printed circuit boards (printed wiring boards, PWB). The epoxy resins used therein have particularly gained popularity because of their ease of processibility. Those epoxy resins also feature good mechanical and chemical properties, such as for example, toughness and resistance to a variety of organic solvents and also display good chemical and moisture resistance. These properties permit the epoxy resin materials to be adapted to diverse application purposes and allow the materials sharing in the composite to be used advantageously.

Generally, the epoxy resins are readily processed into composite materials for PWB applications via the manufacturing of prepregs (B-staging). For example, the substrate material, which is typically an inorganic or organic reinforcing agent in the form of fibers, fleece and fabric or textile materials, is impregnated with the resin. This may be accomplished by coating the substrate with a resin solution in an easily vaporizable or volatilizable solvent. The coating may be carried out by a variety of well-known techniques including rolling, dipping, spraying, and combinations thereof. The prepregs are then heated in an oven chamber to remove solvent and to partially cure the resin. The prepregs obtained after this process must not self-adhere, but they also should not be fully cured. In addition, the prepregs must be sufficiently stable in storage. In the subsequent processing into composite materials, the prepregs must furthermore fuse when there is a rise in temperature and pressure and must bind together under pressure with the reinforcing agents or insertion components as well as with the materials provided for the composite as compactly and permanently as possible; that is the cross-linked epoxy resin matrix must form a high degree of interfacial adherence with the reinforcing agents, as well as with the materials to be bonded together, such as metallic, ceramic, mineral and organic materials.

A key requirement in many applications is the requirement for flame resistance. In many areas, this requirement is given first priority, due to the danger to human beings and material assets, for example in structural materials for airplane and motor vehicle construction and for public transportation vehicles. In electrotechnical and particularly electronic applications, it is absolutely necessary for the electrical laminate materials to be flame resistant, due to the substantial worth of the electronic components assembled thereon and the intrinsic value of human life associated with working on or near devices containing PWB components.

Accordingly, it has been customary in the preparation of epoxy-containing laminates to incorporate into the epoxy resin compositions various additives and/or reactives to improve the flame retardancy of the resulting laminate. Many types of flame retardant substances have been used, however, the most common thus far used commercially have been halogen containing compounds such as tetrabromobisphenol A, prepared by reacting the diglycidyl ether of bisphenol A with tetrabromobisphenol A. Typically, in order to reach the desired fire retardancy level (V-0 in the standard "Underwriters Laboratory" test method UL 94), levels of such bromine-containing flame retardant substances are required that provide a bromine content from 10 weight percent to 25 weight percent based on the total weight in the product.

Generally, halogen-containing fire retardant epoxy resins such as those containing tetrabromo-bisphenol A are considered to be safe and effective. However, there has been increasing interest by some to utilize flame-retarded epoxy systems that are not based on halogen chemistry. It is desirable for these new materials to be able to meet the requirements of fire retardancy and to display the same advantages of mechanical properties, toughness, and solvent and moisture resistance that is offered with the halogenated materials currently used.

One such approach proposed by many researchers has been the use of phosphorus based fire retardants. See for example, EP 0 384 939; EP 0 384 940; EP 0 408 990; DE 4 308 185; DE 4 308 187; WO 96/07685; WO 96/07686; U.S. Pat. No. 5,648,171; U.S. Pat. No. 5,587,243; U.S. Pat. No. 5,576,357; U.S. Pat. No. 5,458,978; and U.S. Pat. No. 5,376,453; all of which are incorporated herein by reference in their entirety. In all of these references, a formulation is formed from the reaction of a flame retardant derived from a phosphorus compound and an epoxy resin, which is then cured with an amino cross-linker such as dicyandiamide, sulfanilamide, or some other nitrogen element containing cross-linker to form the thermosetting polymer network.

Specific examples of commercially available phosphorus-based fire retardant additives include Antiblaze™ 1045 (Albright and Wilson Ltd, United Kingdom) which is a phosphonic acid ester. Phosphoric acid esters have also been used as additives, such as, for example, PX-200 (Diahachi, Japan). Commercially available reactive phosphorus containing compounds that have been disclosed as being suitable for epoxy resins include Sanko HCA and Sanko HCA-HQ (Sanko Chemical Co., Ltd., Japan).

Alkyl and aryl substituted phosphonic acid esters are particularly compatible with epoxy resins. More particularly, $C_1$–$C_4$ alkyl esters of phosphonic acid are of value because they contain a high proportion of phosphorus, and are thus able to impart fire retardant properties upon resins in which they are incorporated. However, the phosphonic acid esters are not satisfactory as a substitute for halogenated flame retardants in epoxy resins for the production of electrical laminates for various reasons. First and foremost of these reasons are the phosphonic acid esters often times impart undesirable properties. For example, the phosphonic acid esters are known plasticizers and thus the laminates formed therefrom tend to exhibit undesirable low glass transition temperatures ($T_g$). An additional drawback is that the use of phosphonic acid esters in amounts sufficient to provide the necessary flame retardancy increases the tendency of the resulting cured epoxy resin to absorb moisture. The moisture absorbency of the cured laminate board is very significant, because laminates containing high levels of moisture tend to blister and fail, when introduced to a bath of liquid solder at temperatures around 260° C., a typical step in the manufacture of printed wiring boards.

Various other phosphorus based flame retardant materials are described in the literature, which are either too expensive or feature certain inferior properties. For example, EP 0 754 728 discloses a cyclic phosphonate as a flame retardant material, which is incorporated into an epoxy resin. However, EP 0 754 728 indicates that this cyclic phosphonate should be present in large quantities, such as in excess of 18 weight percent, in order for the resin system to meet UL 94 V-0. This loading for a phosphonate compound may lead to a depression of the Tg or higher moisture absorption. EP 1 116 774 utilizes a hydrogen phosphinate, 9,10-dihydro-9-oxa-10-phosphaphenanthrene-10-oxide, in conjunction with triphenylphosphine oxide. However, the epoxy resin base requires the use of non-standard epoxy resins; namely a xylene-modified novolak resin and naphthylene aralkyl and biphenyl-modified epoxy resins. WO 99/00451 discloses another flame retardant composition utilizing phosphoric acid esters. Although this composition appears to exhibit improved flame retardant properties at low levels of phosphonic acid ester, there is still a need in the industry for a flame retardant epoxy resin with improved $T_g$ and flame retardant properties. Phosphorus flame retardant additives, in general, can lead to a significant plasticizing effect (U.S. Pat. No. 5,587,243 and references cited therein). Also, in the case of additive compounds, there may be a question of the additives leaching from a thermoset polymer network under processing conditions or over time.

Other methods to impart flame retardancy involve preparation of halogen-free flame retardant epoxy resin compositions using a combination of resinous materials and an inorganic filler, such as aluminum trihydrate (EP 0 795 570 A1) or magnesium hydroxide (JP 2001213980 A2). These materials could potentially render the processing of the epoxy resins more difficult, as they are insoluble in the resin systems. Additionally, fairly large load levels are usually required, which can detract from the properties. See, generally, U.S. Pat. No. 6,097,100 and references cited therein for a description of various inorganic fillers; and WO 01/42359.

Various other phosphorus compounds have also been used to prepare halogen-free flame retardant epoxy resins useful in the manufacture of composite materials. For example, the use of phosphorus-carbon bonded moieties, such as phosphine oxides, have been disclosed in WO 01/42253; U.S. Pat. No. 4,345,059; EP 1 116 774; and JP2000186186; all of which are incorporated herein by reference in their entirety. A key disadvantage of these compositions, however, is that they are costly to prepare, because they utilize unique raw materials. For example, JP2000186186 discloses the use of pure bis(p-hydroxyphenyl)phenyl-phosphine oxide, which requires the use of a pure dichlorophenyl phosphine. In an analogous manner, the phosphine oxides utilized in WO 01/42253 require lithium reagents and cryogenic reaction conditions, thus warranting special equipment for its manufacture. The phosphine oxides display benefits of improved resistance to moisture uptake when compared with other phosphorus compounds that contain P—O bonded moieties, as disclosed in WO 01/42253.

Thus, it is an object of this invention to provide economical yet useful phosphine oxide compounds for the manufacture of non-halogen epoxy resins having utility in the manufacture of composite materials, such as electrical laminates for printed wiring boards or printed circuit boards.

It is yet an other object of this invention to provide phosphine oxide containing, hydrolytically and thermally stable, non-halogenated, flame resistant epoxy resin compositions, which are used for making laminates for printed wiring boards and various other composite materials.

Further, it is also an object of this invention to provide phosphine oxide containing epoxy resin compositions having improved flammability reductions when compared with bisphenol A based epoxy laminates.

Finally, it is an object of this invention to provide halogen free phosphine oxide containing epoxy resin compositions that are useful as replacements for tetrabromobisphenol A in FR-4 laminate applications.

These and other objects and advantages of the invention will be seen from the following detailed description.

SUMMARY OF THE INVENTION

The present invention is directed to novel mixtures of hydroxyarylphosphine oxides, their use in epoxy compositions and methods of producing them. There is thus provided in one aspect of the invention a mixture of hydroxyarylphosphine oxides comprising:

(a) a mono(hydroxyaryl)phosphine oxide of the formula:

(I)

wherein $R_1$ is a divalent, substituted or unsubstituted arylene moiety and $R_2$ is a monovalent substituted or unsubstituted aryl moiety or is an alkyl moiety or is an aralkyl moiety; and (b) a bis(hydroxyaryl)phosphine oxide of the formula:

(II)

wherein $R_1$ and $R_2$ are defined as above; and (c) a tris(hydroxyaryl)phosphine oxide of the formula:

(III)

wherein $R_1$ is defined as above; and (d) optionally containing minor amounts of a pentavalent phosphine oxide of the formula:

(IV)

wherein $R_2$ is defined as above. The present invention likewise includes the corresponding alkoxyaryl ether mixtures and their derivatives where the hydroxyaryl moiety is replaced by a methoxyaryl, propoxyaryl, butoxyaryl or other $C_1$–$C_6$ (1 carbon to 6 carbon) alkoxyaryl substitution on the phosphine oxide nucleus.

In yet another aspect of this invention mixtures of glycidyl ethers derived from a mixture of hydroxyarylphosphine oxides described herein are provided.

Yet in another aspect of this invention novel curable flame retardant epoxy compositions derived from the novel hydroxyaryl phosphine oxides or the glycidyl ethers of this invention are provided.

In another aspect of this invention novel bis(hydroxyphenyl)phosphine oxides of the Formula (V) and novel diglycidyl ethers of the formula (VI) are provided.

including phenyl, in the case of compound VI.

In another aspect of this invention a triglycidyl ether of the following formula is also provided.

In further aspects of this invention, a series of curable epoxy compositions comprising a combination of novel bis(hydroxyaryl)phosphine oxides of this invention, and novel reaction adducts of mono-, bis-, tris(hydroxyaryl) phosphine oxide mixtures with curable epoxy resins is provided. The curable epoxy resins may include, for (V)

(VI)

Wherein n=0–100, preferably 0–20, most preferably 0–5; and wherein —R is selected from the group consisting of example, but are not limited to, epoxy novolak type resins and/or diglycidyl ethers of bisphenol A and bisphenol F. Additionally, mono-, bis, tris(glycidoxyaryl)phosphine oxide mixtures and novel bis(glycidoxyaryl)phosphine oxides of this invention are described, which can act as curable epoxy resins. Resin-impregnated composites comprising the curable flame retardant epoxy compositions described herein are additionally provided.

BRIEF DESCRIPTION OF DRAWINGS

The invention is described in detail below with reference to the drawings wherein like numerals designate similar parts and the invention is described in connection with numerous examples. In the drawings.

DETAILED DESCRIPTION OF THE INVENTION

As used herein, the term "arylene" refers to a divalent aromatic substituent radicals covalently bonded to the phosphorous atom by way of an aromatic carbon including phenylene, biphenylene, naphthylene, and the like; the term "aryl" refers to corresponding monovalent aromatic substituent radicals covalently bonded to the phosphorous atom by way of an aromatic carbon including phenyl, biphenyl, naphthyl, and the like; substituted analogs thereof means said arylene moiety or aryl moiety is substituted by at least one suitable substituent group selected from the group consisting of straight or branched alkoxy group such as methoxy, straight or branched alkyl and/or fluoroalkyl group such as methyl, trifluoromethyl, alkenyl group such as vinyl, and the like, provided that such substituent does not interfere with the ability of the phosphorus compound to react with the epoxy resin. Thus, for example, when $R_1$ is phenylene, examples of suitable substituted $R_1$ are o, m or p-hydroxy-methyl-phenyl or commonly known as o-cresyl, m-cresyl, or p-cresyl; and so forth.

"Alkyl" means a straight chain, branched or cyclic saturated substituent typically of 1–20 carbon atoms including methyl, ethyl, propyl substituents and so forth; whereas "aralkyl" and like substituents are characterized by bonding to the nucleus through a saturated carbon and including aromatic structures. Such substituents include phenylpropyl or phenylbutyl substituents and so forth.

Thus in accordance with the practice of this invention there is provided novel mixtures of hydroxyarylphosphine oxides, their use in epoxy compositions and methods of producing them. The curable epoxy compositions so formed are particularly useful in the manufacture of laminates that are suitable in the production of printed circuit boards or printed wiring boards.

There is thus provided in one aspect of the present invention a mixture of hydroxyarylphosphine oxides comprising:

(a) a mono(hydroxyaryl)phosphine oxide of the formula:

(I)

wherein $R_1$, is a divalent, substituted or unsubstituted arylene moiety and $R_2$ is a monovalent, substituted or unsubstituted aryl moiety or is an alkyl moiety or is an aralkyl moiety; and

(b) a bis(hydroxyaryl)phosphine oxide of the formula:

(II)

wherein $R_1$ and $R_2$ are defined as above; and (c) a tris(hydroxyaryl)phosphine oxide of the formula:

(III)

wherein $R_1$ is defined as above; and (d) optionally containing minor amounts of a pentavalent phosphine oxide of the formula:

(IV)

wherein $R_2$ is defined as above.

In one of the embodiments of this invention, $R_1$ in the above formulae is derived from an alkyl aryl ether. Examples of such starting materials include methoxyphenyl-, 4-methoxynaphthyl-, o-methoxycresyl- and so forth.

In another embodiment of this aspect of the invention, the mixture is consisting essentially of diphenyl(4-hydroxyphenyl)phosphine oxide, bis(4-hydroxyphenyl)phenylphosphine oxide and tris(4-hydroxyphenyl)phosphine oxide, said mixture optionally including minor amounts of triphenylphosphine oxide.

In a preferred embodiment of this invention, the mixture comprises from about 10 to about 50 mole percent of the mono(hydroxyaryl)phosphine oxide of the formula (I), from about 30 to about 60 mole percent of the bis(hydroxyaryl) phosphine oxide of the formula (II), from about 10 to 50 mole percent of the tris(hydroxyaryl)phosphine oxide of the formula (III) and from about 0 up to about 10 mole percent of the pentavalent phosphine oxide of the formula (IV).

In another aspect of this invention there is also provided a mixture of glycidyl ethers derived from a mixture of hydroxyarylphosphine oxides by way of reacting the mixture of hydroxyarylphosphine oxides described herein with epichlorohydrin. Such reactions can be carried out by any of the well-known techniques in the art. The molecular weights (or EEW) of the product glycidoxyarylphosphine oxide mixtures can be affected by varying the stoichiometry of the epichlorhydrin used in the reaction with the mixture of hydroxyarylphosphine oxides described herein. Alternatively, the lower molecular weight glycidoxyarylphosphine oxide mixtures can be advanced with the described hydroxyarylphosphine oxide mixtures of this invention to obtain a desired molecular weight or EEW.

A preferred method of making the mixture of hydroxyarylphosphine oxides includes (a) preparing a mixed Grignard reaction mixture including the species $(R_1)$ MgX and (R$_2$)MgX wherein R$_1$, is an arylalkylether radical and R$_2$ is an aryl or alkyl or aralkyl radical, X representing a halogen atom; (b) reacting the mixed Grignard reaction mixture with phosphorous oxychloride to produce a mixture of arylalkyletherphosphine oxides; and (c) converting the mixture of arylalkyletherphosphine oxides to the mixture of hydroxyarylphosphine oxides, noted above. A suitable method of converting the arylalkylethers to arylhydroxides involves treatment with HBr, HI or HCl in the presence of a metal halide salt.

This invention utilizes, in a general sense, the use of a mixed Grignard reagent system to produce a mixture of phosphine oxides. This invention can be applied to a wide array of compounds wherein an arylmagnesium halide can be mixed with an alkoxyarylmagnesium halide and reacted with phosphorus oxychloride, or alternatively, an alkylmagnesium halide can be reacted with phosphorus oxychloride in tandem with an alkoxyarylmagnesium halide. The generalized approach is to use a main Grignard reagent that contains a functional group that can be chemically transformed to a group capable of reacting with a wide variety of active intermediates, and furthermore, using a second Grignard reagent that is functionally inert. The relative stoichiometry between the two Grignard reagents and the phosphorus oxychloride can be adjusted to affect the distribution of the mixtures in the desired fashion at will. The two Grignard reagents can be premixed and reacted with the phosphorus oxychloride together, or the reagents can be added to the phosphorus oxychloride in a serial fashion, depending on the requirements of the particular reaction. Alternatively, phosphorus trichloride can be used in place of phosphorus oxychloride in the reaction, followed by oxidizing the resulting phosphine to phosphine oxide by standard synthetic procedures.

Alternatively, a wide array of organometallic reagents and intermediates can be used to effect the product mixture distribution in place of the magnesium approach. These reagents are, for example, but not limited to: organozincs, -sodium, -lithium, -potassium, and transition metal facilitated routes in general, which are known to one skilled in the art.

The invention pertains, in a preferred aspect, to the substances obtained by a two step process. The first step involves the reaction of phosphorus oxychloride with a novel mixture of phenylmagnesium bromide and 4-methoxyphenylmagnesium bromide. The reaction produces a further novel mixture of four products; triphenylphosphine oxide, diphenyl(4-methoxyphenyl) phosphine oxide, di(4-methoxyphenyl)phenylphosphine oxide, and tri(4-methoxyphenyl)phosphine oxide. The preparation of these mixtures has the added benefit of being much more economical to produce than making the pure materials, which require more expensive reagents. Surprisingly, the amount of triphenylphosphine oxide produced in the reaction can be controlled by the Grignard reagent stoichiometric ratio to a near negligible level. This product mixture can then be reacted with concentrated hydrobromic acid in the presence of a catalytic amount of a metal halide to produce the corresponding mixture of free phenols: triphenylphosphine oxide, diphenyl(4-hydroxyphenyl)phosphine oxide, di(4-hydroxyphenyl) phenylphosphine oxide, and tri(4-hydroxyphenyl)phosphine oxide. Additionally, the neutral material could be removed by washing techniques if so desired.

In addition, the unsubstituted phenyl group in the product, as described above in the preferred aspect, for example, can be replaced by substituting bromobenzene with another aryl or alkyl halide. Examples of aryl halides include, but are not limited to 1-bromonapthylene; 2-bromonaphthylene; 4-bromotoluene; 4-bromophenoxybenzene; and 5-bromo-1,2,4-trimethylbenzene. Examples of alkyl halides include, but are not limited to, methyl bromide and tert-butyl bromide. The reactive groups for the final product mixture, in the most preferred case, would be the epoxy group or hydroxyl group, which could then be made to react with epoxy resins as a reactive diluent in the co-cure or as a pre-reacted intermediate, or as a curing agent directly. It is recognized that other functional groups could also be used. This lower cost approach produces a distribution of products in the product mixture.

The product distribution in the mixtures also facilitates generalized advancement in epoxy resins. Curable, flame retardant epoxy resins suitable for use in the manufacture of resin formulations, prepregs, and laminates can be prepared from the forwarding reaction of the stated mixture with a commercially available epoxy resin. The product distribution enables certain physical characteristics to be easily affected in the cured and uncured resin. The properties involved are, for example, but not limited to, molecular weight, viscosity, glass transition temperature, and gel point. The reasons for this are related to the number of aromatic hydroxyl groups present in each reactive species. Using a specific case as an example, the di(4-hydroxyphenyl) phenylphosphine oxide reacts linearly with an epoxy resin in the normal fashion as in the commercially used tetrabromobisphenol A. However, tri(4-hydroxyphenyl)phosphine oxide can react with a bifunctional epoxy resin as a cross linking agent to give a cross linked thermoset. The presence of diphenyl(4-hydroxyphenyl)phosphine oxide off sets this characteristic by acting as a chain termination agent. This product mixture reacts readily with epoxide groups in standard epoxy resins without the need of a catalyst, such as a phosphonium salt. This reaction occurs readily at elevated temperatures, in the range of 100 to 200° C. A wide range of molecular weights can be obtained in the copolymer product resins by use of the appropriate reaction stoichiometry.

Representative epoxy resins suitable for use in the present invention are presented in *Epoxy Resins Chemistry and Technology, Second Edition* edited by Clayton A. May (Marcel Dekker, Inc. New York, 1988), *Chemistry and Technology of Epoxy Resins* edited by B. Ellis (Blackie Academic & Professional, Glasgow, 1993), *Handbook of Epoxy Resins* by H. E. Lee and K. Neville (McGraw Hill, New York, 1967), and EP 1116774 A2. Suitable epoxy resins are, but not limited to, epoxy resins based on bisphenols and polyphenols, such as, bisphenol A, tetramethylbisphenol A, bisphenol F, bisphenol S, tetrakisphenylolethane, resorcinol, 4,4'-biphenyl, dihydroxynaphthylene, and epoxy resins derived from novolaks, such as, phenol:formaldehyde novolak, cresol:formaldehyde novolak, bisphenol A novolak, biphenyl-, toluene-, xylene, or mesitylene-modified phenol:formaldehyde novolak, aminotriazine novolak resins and heterocyclic epoxy resins derived from p-amino phenol and cyanuric acid. Additionally, aliphatic epoxy resins derived from 1,4-butanediol, glycerol, and dicyclopentadiene skeletons, are suitable, for example. Many other suitable epoxy resin systems are available and would also be recognized as being suitable by one skilled in the art.

It is generally advantageous to use an epoxy resin which possesses on average more than 1 and preferably at least 1.8, more preferably at least 2 epoxy groups per molecule. In the broadest aspect of the invention, the epoxy resin may be any saturated or unsaturated aliphatic, cycloaliphatic, aromatic or heterocyclic compound which possesses more than one 1,2-epoxy group. Examples of heterocyclic epoxy compounds are diglycidylhydantoin or triglycidyl isocyanurate (TGIC).

The epoxy resin is preferably one that has no lower alkyl aliphatic substituents, for example the glycidyl ether of a phenol novolak, or the glycidyl ether of bisphenol-F. Preferred epoxy resins are epoxy novolak resins (sometimes referred to as epoxidized phenolic novolak resins, a term which is intended to embrace both epoxy phenol novolak resins and epoxy cresol novolak resins).

Epoxy novolak resins (including epoxy cresol novolak resins) are readily commercially available, for example, under the trade names D.E.N.™, Quatrex™, (Trademarks of the Dow Chemical Company), and Epon™ (trademark of Resolution Performance Products). The materials of commerce generally comprise mixtures of various glycidoxyphenyl and methyl-, ethyl- propyl- glycidoxyphenyl groups.

The arylalkyletherphosphine oxide mixtures or the corresponding hydroxyaryl-phosphine oxide mixtures of the present invention can be applied for use as flame retardants for a vast array of thermosetting and thermoplastic resins, such as polycarbonates, polyesters, vinyl esters, cyanate esters, polyamides, polyimides, polyurethanes, and many others; but more specifically, to the flame retardation of epoxy resins as a general approach. In addition, the deprotection of alkylaryl ethers generates an alkyl halide, which is a value-added product.

These mixtures, containing hydroxy substituents, may be converted to any number of functional groups by those skilled in the art, such as; but not limited to, ethers, carbonates, carbamates, and esters to modify the properties of the materials to improve the compatibility in a given resin system. In particular, these mixtures may be converted to the corresponding glycidyl ether derivatives or the phenolic mixtures can be used directly as a cross-linking agent in epoxy resin formulations. The hydroxyphenyl mixtures, which may be chemically converted into epoxy oligomers by reaction with commercially available epoxy resins or epichlorohydrin, or the glycidyl ether mixtures are intended for flame retardant printed wiring boards.

These mixtures, containing hydroxy substituents, can also be converted to phosphorus-containing oligomers and polymers such as, but not limited to polycarbonates, polyesters, polyurethanes, polyimides, and vinyl esters, which would also act as flame retardants.

Furthermore, the product mixture can also be converted to the glycidyl ether derivatives by reaction with epichlorohydrin and a base as described above. The glycidyl ether derivatives can then also be used as a co-reactive in epoxy resin formulations intended for flame retardation applications. This approach can lead to a significantly higher level of phosphorus in the resin system. Furthermore, the glycidyl ether phosphine oxide mixtures can be advanced with hydroxyl phosphine oxides of this invention to make oligomers.

Alternative methods to obtain the glycidyl ethers are available and could also be employed. For example, the hydroxyarylphosphine oxide mixture can be converted to the allyl ether by treatment with allyl chloride, followed by oxidation of the resulting olefin to an epoxy group by known synthetic methods.

The phosphine oxide mixture, or after being converted to the glycidyl ethers, or after being advanced to epoxy oligomers, can be cured with standard hardeners such as a combination of dicyandiamide and 2-methylimidazole. The phenolic mixtures act as hardeners themselves. Other phenolic hardeners include, but not limited to, phenolic resins obtained from the reaction of phenols or alkyl-substituted phenols with formaldehyde, such as phenol novolaks, cresol novolaks, and resoles. Other hardeners include amines, anhydrides, and combinations involving amines with Lewis acids. Amine hardeners include, but not limited to, alkyl amines, aryl amines, amides, biguanide derivatives, melamine and guanamine derivatives, methylene-dianiline, diaminodiphenylsulfone, imidazoles, ethylenediamine, diethylenetriamine, polyamides, polyamidoamines, imidazolines, polyetheramines, araliphatic amines, dicyandiamide, and m-phenylenediamine. Combinations of nitrogen-containing catalyst with Lewis acids include the heterocyclic secondary and tertiary amines and the Lewis acids including oxides and hydroxides of zinc, tin, silicon, aluminum, boron, and iron. Other curing agents include carboxylic acids and anhydrides, amino-formaldehyde resins, and amine-boron complexes. Many types of curing agents that would be useful can be found in any basic epoxy resin text. In addition, the resins described in the present invention (see Example 3a for a specific case) may be formulated with additional additives and fillers to affect cure rate, enhance flame retardancy, and increase physical properties. The formulation in Example 6 is intended to be used for the manufacture of prepregs and glass-reinforced laminates for the fabrication of printed wiring boards.

Typically, fillers and reinforcing agents include mica, talc, kaolin, bentonite, wollastonite, glass fiber, glass fabrics glass matt, milled glass fiber, glass beads (solid or hollow), silica, or silicon carbide whiskers and so forth. Many of these materials are enumerated in the *Encyclopedia of Materials Science and Engineering*, Vol. # 3, pp. 1745–1759, MIT Press, Cambridge, Mass. (1986), the disclosure of which is incorporated herein by reference. Combinations of fillers are preferred in some embodiments; whereas in other embodiments, the reinforcing agent makes up most of the composite of the invention, as in the case of glass fabric used in prepregs and laminates for printed wiring boards.

Additionally, the resin described in the present invention (see Example 3a for a specific case) may be formulated with other flame-retardant materials as co-additives with the compounds of the present invention to improve the performance. These co-FR materials could be either inorganic or organic and can be reactive or additive based compounds. Examples of inorganic additive type materials include, but not limited to, aluminum trihydrate (ATH), magnesium hydroxide, barium hydroxide, calcium carbonate, titanium dioxide, and silicon dioxide. Examples of organic based additives or reactives include, but not limited to, triphenyl phosphate, resorcinol bis(di-2,6-xylyl phosphate), 9,10-dihydro-9-oxa-10-phosphaphenanthrene-10-oxide, bisphenol A bis(diphenyl-phosphate), melamine, melamine phosphate, melamine borate and many others familiar to one skilled in the art.

The preparation of the mixtures of the present invention has the added benefit of being much more economical to produce than making the pure materials from pure intermediates, which consequently, requires more expensive reagents. As in, for example, one method in the preparation of bis(4-methoxyphenyl)phenylphosphine oxide, which could entail the use of dichlorophenylphosphine oxide. The raw materials used in this specific invention are based on the relatively inexpensive phosphorus oxychloride and organo halides. Alternatively, one could utilize phosphorus trichloride in the same type of chemistry and oxidize the resulting phosphines to phosphine oxides by known synthetic methods.

To demonstrate the flame retardant activity of these mixtures, a series of laminates was prepared using various forms of the preferred invention. A study was undertaken in order to observe the intrinsic properties of the reactive phosphine oxide and its derivatives upon the resulting laminates when using a bisphenol A based epoxy resin without the use of any additional additives other than a standard hardener and accelerator (see Examples below, particularly, Example 7, Table 3). Significant improvements in the flame retardant properties are observed with the compositions of this invention. In addition, improved thermomechanical properties are attained, such as improved thermal stability and good glass transition temperatures of the resulting laminates, while offering significant advantages in cost savings.

Figure 1:
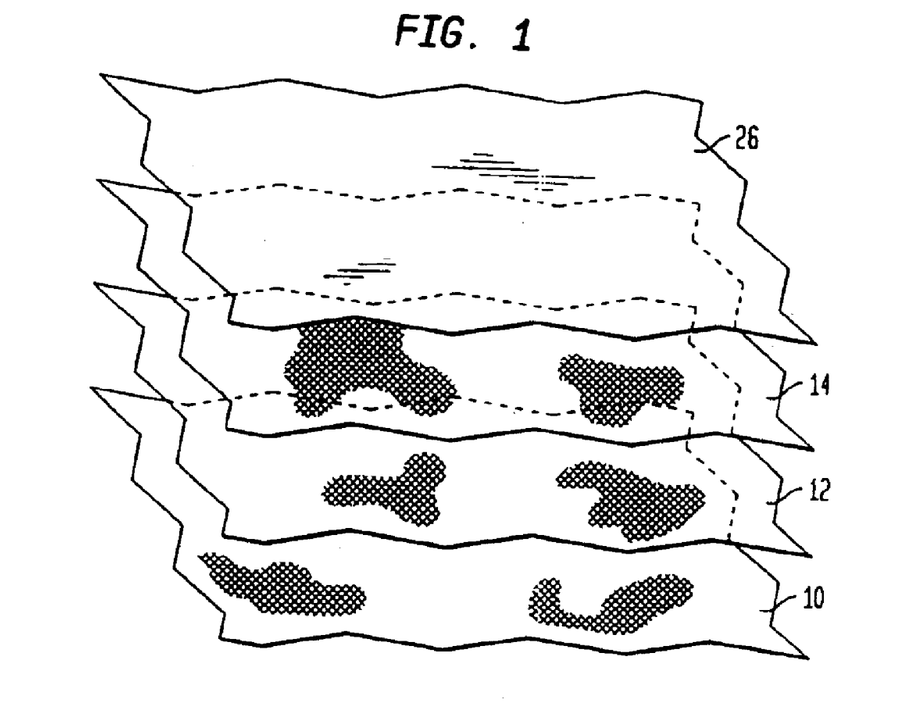
FIG. 1 is a perspective exploded schematic view showing a plurality of resin-impregnated glass cloth layers and a copper foil layer of the class used to make printed wiring boards.

Thus in accordance with the practice of this invention a resin-impregnated composite comprising at least one of a filler or reinforcing agent and the curable composition as described herein is provided, which is at least partially cured. For example, the glycidyl ethers and epoxy resins of the invention are advantageously used in the fabrication of prepregs and laminates used to make printed wiring boards. The resin prepared as described herein is mixed with one or more hardener(s) and optionally accelerator(s) and applied to a glass cloth, such as glass cloth layers 10, 12, 14 as shown in FIG. 1. The resin-impregnated sheets or prepregs are then at least partially cured in an oven typically at 150° C.–200° C. for a few minutes; for example, from 1–5 minutes.

Figure 2:
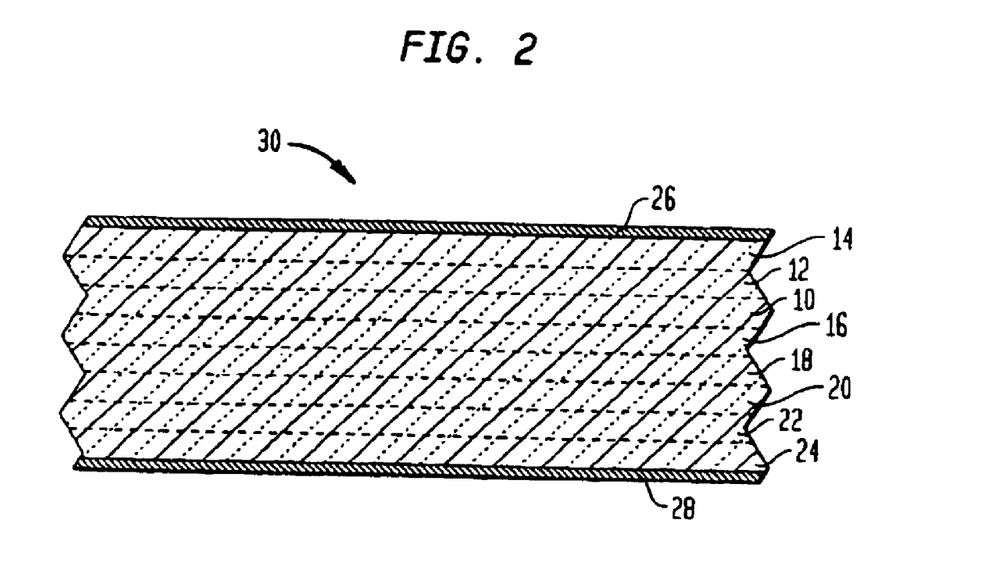
FIG. 2 is a schematic view in sectional elevation of a heat-pressed copper clad laminate of the class used to make printed wiring boards including a plurality of intermediate strata formed from glass prepregs which have been heat-cured into a substantially integrated structure generally inseparable into its constituent layers.

In order to prepare a laminate of the class used for printed wiring boards, a plurality of prepregs are stacked next to each other as shown in FIG. 2, wherein resin-impregnated layers 10–24 are shown. On each side of the stack there is provided a copper foil layer, such as layers 26, 28. The stack, including cloth layers 10–24 and foil layers 26, 28, is then pressed at elevated temperatures in a press for an hour or more to produce a consolidated laminate 30. Laminate 30 thus includes a plurality of fused layers 10–24 of the resin-impregnated glass fabric. If so desired, more or fewer layers of prepregs or foil may be used depending on the desired structure.

In another embodiment of this invention, there is also provided a novel bis(hydroxyphenyl)phosphine oxide of the formula:

(V)

wherein —R is selected from the group consisting of

Specific examples of di(4-hydroxyphenyl)(aryl or alkyl) bisphenols, as disclosed herein include di(4-hydroxyphenyl)-α-naphthylphosphine oxide, di(4-hydroxyphenyl)-β-naphthylphosphine oxide, di(4-hydroxyphenyl)-tert-butylphosphine oxide, di(4-hydroxyphenyl)-2,4,5-trimethylphenylphosphine oxide, di(4-hydroxyphenyl)-4-phenoxyphenylphosphine oxide and di(4-hydroxyphenyl)-p-tolylphosphine oxide.

In another aspect of this embodiment of the invention, the bisphenols as described herein can also be converted to the corresponding bis-glycidyl ethers by way of reaction with epichlorohydrin in the presence of base as described hereinabove. Both the bisphenols and their bis-glycidyl ethers are suitable in the formation of curable epoxy formulations as described herein, which are further employed in the formation of fire retardant laminates as described herein.

This invention is further illustrated by the following examples, which are provided for illustration purposes and in no way limit the scope of the present invention.

EXAMPLES (GENERAL)

In the Examples that follow, the following abbreviations are used:

| | |
|---|---|
| BHPPPOM | bis(4-hydroxyphenyl)phenylphosphine oxide mixture |
| CDCl$_3$ | deutero-chloroform |
| DICY | dicyandiamide |
| d$_6$-DMSO | d$_6$-dimethylsulfoxide |
| DSC | differential scanning calorimetry |
| EEW | epoxide equivalent weight |
| EPON 828 | Resolution Performance Products; 4,4'-isopropylidenediphenol polymer with 1-chloro-2,3-epoxypropane |
| FR | flame retardant |
| GC | gas chromatograph |
| LC | liquid chromatograph |
| MeCN | acetonitrile |
| MI | 2-methylimidazole |
| MW | molecular weight |
| NMR | nuclear magnetic resonance spectroscopy, usually of phosphorus, $^{31}$P |
| T-260 | refers to a test method defined by the IPC (Association Connecting Electronics Industries) to determine the time to delamination at 260° C. Test method No. 2.4.24.1 is used. |
| PGME | Dowanol PM (the chemical used is 1-methoxy-2-propanol) |
| POCl$_3$ | phosphorus oxychloride |
| PWB | printed wiring boards |
| rt | room temperature |
| T$_g$ | glass transition temperature |
| TGA | thermal gravimetric analysis |
| THF | tetrahydrofuran |
| TPPO | triphenylphosphine oxide |

Example 1

Pure Hydroxyarylphosphine Oxides

1a. Bis(4-methoxyphenyl)phenylphosphine Oxide.

A slurry of magnesium (133.7 g, 5.50 mol), tetrahydrofuran (988 g), and 1,2-dibromoethane (0.1 g, 0.5 mmol) was refluxed for 20 min. under a blanket of nitrogen. 4-Bromoanisole (1002 g, 5.357 mol) was added by drop over 6 h at a rate to maintain 70° C. The reaction mixture was heated for an additional hour. Dichlorophenylphosphine oxide (479.4 g, 2.459 mol) was added by drop to maintain a temperature of 35° C. over 5 h. The reaction mixture was worked up to give bis(4-methoxyphenyl)phenylphosphine oxide (770.8 g, 93% yield) as a viscous amber oil. $^{31}$P NMR: ($d_6$-DMSO) δ 30.2 (s).

1b. Bis(4-hydroxyphenyl)phenyl phosphine Oxide.

Bis(4-methoxyphenyl)phenyl phosphine oxide (1.77 g, 5.2 mmol) and hydrobromic acid (31.0 g, 48%, 0.18 mol) were stirred at 123° C. for 21 h. The flask was fitted with a sodium sulfite scrubber for containment of methyl bromide. The reaction mixture was worked up to give the product as a tan powder (1.0 g, 62% yield). $^{31}$P NMR: ($d_6$-DMSO) δ 27.9 (s).

1c. Tris(4-methoxyphenyl)phosphine Oxide.

A reaction flask under nitrogen containing magnesium turnings (223.9 g, 9.21 mol) and 1950 mL THF was charged with 1 drop of 1,2-dibromoethane and heated to reflux for 1 h. Heating was removed and p-bromoanisole (1683 g, 9.00 mol) was added dropwise at a rate to maintain reflux. After holding the reaction mixture overnight, POCl$_3$ (460.0 g, 3.00 mol) was added slowly over 2 h at 50–79° C. and the resulting mixture was held overnight at 50° C. The product was isolated by aqueous workup to give 984.5 g of tris(4-methoxyphenyl)phosphine oxide (89.0% yield). Recrystallized analytical specimen (from ethyl acetate): mp 145.2° C. (DSC), lit. 143–144° C. (*J. Org. Chem.* 1960, 25, 2001).

1d. Tris(4-hydroxyphenyl)phosphine Oxide.

A reaction flask containing tris(4-methoxyphenyl)phosphine oxide (973.2 g) was charged with 48% aq HBr (2250 mL) and KBr (126.1 g). The flask was fitted with a sodium sulfite scrubber for containment of methyl bromide. The reaction mixture was heated to reflux (114° C.) and maintained at reflux until complete based on HPLC analysis. The product was worked up to give 558.5 g of tris(4-hydroxyphenyl)phosphine oxide ($^{31}$P NMR ($d_6$-DMSO): δ 27.6 (s); $^1$H NMR ($d_6$-DMSO): δ 10.9 (s, 3H), 7.38 (m, 6H), 6.84 (m, 6H)).

Following the procedures as set out in Example 1a various methoxyaryl phosphine oxides of this invention are prepared employing the starting materials as summarized below:

1e. Bis(4-methoxyphenyl)(1-naphthyl)phosphine oxide:

| | |
|---|---|
| Magnesium | 133.7 g, 5.50 mol |
| THF | 988 g |
| 1,2-dibromoethane | 0.1 g, 0.5 mmol |
| 4-Bromoanisole | 1002 g, 5.357 mol |
| Dichloro(1-naphthyl)phosphine oxide | (612.5 g, 2.5 mol) |

1f. Bis(4-methoxyphenyl)(2-naphthyl)phosphine oxide:

| | |
|---|---|
| Magnesium | 133.7 g, 5.50 mol |
| THF | 988 g |
| 1,2-dibromoethane | 0.1 g, 0.5 mmol |
| 4-Bromoanisole | 1002 g, 5.357 mol |
| Dichloro(2-naphthyl)phosphine oxide | (612.5 g, 2.5 mol) |

1g. Bis(4-methoxyphenyl)(4-methylphenyl)phosphine oxide:

| | |
|---|---|
| Magnesium | 133.7 g, 5.50 mol |
| THF | 988 g |
| 1,2-dibromoethane | 0.1 g, 0.5 mmol |
| 4-Bromoanisole | 1002 g, 5.357 mol |
| Dichloro(4-methylphenyl)phosphine oxide | (522.5 g, 2.5 mol) |

1h. Bis(4-methoxyphenyl)-2,4,5-trimethylphenylphosphine oxide:

| | |
|---|---|
| Magnesium | 133.7 g, 5.50 mol |
| THF | 988 g |
| 1,2-dibromoethane | 0.1 g, 0.5 mmol |
| 4-Bromoanisole | 1002 g, 5.357 mol |
| Dichloro-(2,4,5-trimethylphenyl)phosphine oxide | (592.7 g, 2.5 mol) |

1i. Bis(4-methoxyphenyl)(4-phenoxyphenyl)phosphine oxide:

| | |
|---|---|
| Magnesium | 133.7 g, 5.50 mol |
| THF | 988 g |
| 1,2-dibromoethane | 0.1 g, 0.5 mmol |
| 4-Bromoanisole | 1002 g, 5.357 mol |
| Dichloro(4-phenoxyphenyl)phosphine oxide | (677.7 g, 2.5 mol) |

1j. Bis(4-methoxyphenyl)-tert-butylphosphine oxide:

| | |
|---|---|
| Magnesium | 133.7 g, 5.50 mol |
| THF | 988 g |
| 1,2-dibromoethane | 0.1 g, 0.5 mmol |
| 4-Bromoanisole | 1002 g, 5.357 mol |
| Dichloro-tert-butylphosphine oxide | (437.5 g, 2.5 mol) |

Following the procedures as set out in Example 1b various hydroxyaryl phosphine oxides of this invention are prepared employing the starting materials as summarized below:

1l. Bis(4-hydroxyphenyl)(1-naphthyl)phosphine oxide:

| | |
|---|---|
| Bis(4-methoxyphenyl)(1-naphthyl)phosphine oxide | 2.42 g, 5.2 mmol |
| Hydrobromic acid | 31.0 g, 48%, 0.18 mol |

1m. Bis(4-hydroxyphenyl)(2-naphthyl)phosphine oxide:

| | |
|---|---|
| Bis(4-methoxyphenyl)(2-naphthyl)phosphine oxide | 2.42 g, 5.2 mmol |
| Hydrobromic acid | 31.0 g, 48%, 0.18 mol |

1n. Bis(4-hydroxyphenyl)(4-methylphenyl)phosphine oxide:

| | |
|---|---|
| Bis(4-methoxyphenyl)(4-methylphenyl)phosphine oxide | 1.8 g, 5.1 mmol |
| Hydrobromic acid | 31.0 g, 48%, 0.18 mol |

1o. Bis(4-hydroxyphenyl)(2,4,5-trimethylphenyl)phosphine oxide:

| | |
|---|---|
| Bis(4-methoxyphenyl)(2,4,5-trimethylphenyl)phosphine oxide | 1.94 g, 5.1 mmol |
| Hydrobromic acid | 31.0 g, 48%, 0.18 mol |

1p. Bis(4-hydroxyphenyl)-tert-butylphenylphosphine oxide:

| | |
|---|---|
| Bis(4-methoxyphenyl)-tert-butylphenylphosphine oxide | 1.65 g, 5.2 mmol |
| Hydrobromic acid | 31.0 g, 48%, 0.18 mol |

Example 2

Dihydroxyarylphosphine Oxide Mixtures

2a. Bis(4-methoxyphenyl)phenylphosphine Oxide Mixture.

Magnesium (1430 g, 58.8 mol), tetrahydrofuran (12 L), and 1,2-dibromoethane (2.2 g, 0.012 mol) were stirred under nitrogen for 1 h. The mixture was then heated to reflux and then the heating stopped. Bromobenzene (3000 g, 19.1 mol) and 4-bromoanisole (7150 g, 38.2 mol) were added consecutively at a rate to maintain a slow reflux (67° C.) over a period of 4 h. The reaction mixture was then held for a further 5 h at 70° C. Phosphorus oxychloride (2930 g, 19.1 mol) was added at a rate to maintain a temperature of 70° C. (5 h). The reaction was then held at 70° C. for a further 5 h. The reaction mixture was quenched and worked up to give the product mixture (5772 g, 89%) as an amber colored oil. $^{31}$P NMR: ($d_6$-DMSO) δ 26.9 (s, 6%), 26.8 (s, 23%), 26.6 (s, 44%), 26.5 (s, 27%). GC (area %): triphenylphosphine oxide 3.8%, diphenyl(4-methoxyphenyl)phosphine oxide 21.5%, bis(4-methoxyphenyl)phenylphosphine oxide 40.6%, and tris(4-methoxyphenyl)phosphine oxide 25.7%.

2b. Bis(4-hydroxyphenyl)phenylphosphine oxide mixture.

Bis(4-methoxyphenyl)phenylphosphine oxide mixture (2359 g, 6.97 mol), hydrobromic acid (48%, 8344 g, 49.5 mol), and potassium bromide (243 g, 2.04 mol) were stirred at 120° C. for 48 h. The flask was fitted with a sodium sulfite scrubber for containment of methyl bromide. The lower aqueous layer was removed and the product layer was worked up to afford bis(4-hydroxyphenyl)phenylphosphine oxide mixture as a tan powder (1601 g, 74%). m.p. (DSC): 93° C. $^{31}$P NMR ($d_6$-DMSO): δ 27.7 (s, 24.7%); 27.5 (s, 47.7%); 27.4 (s, 25.4%); 27.2 (s, 2.2%).

The mixed Grignard reaction was performed using varying stoichiometries of Grignard reagent (Table 1.). The product ratios were determined by use of $^{31}$P NMR. Entry 2 was discussed in example text.

TABLE 1

Mixed Grignard Reaction Using different Reagent Ratios.

| Entry | PhMgBr Equiv. | MeOPhMgBr Equiv. | POCl$_3$ Equiv. | % Yld. | Mol % from $^{31}$P NMR | | | |
|---|---|---|---|---|---|---|---|---|
| | | | | | TPPO[1] | Mono[2] | Bis[3] | Tris[4] |
| 1 | 0.60 | 2.4 | 1 | 85 | 0 | 9.7 | 38.3 | 52.0 |
| 2 | 1.0 | 2.0 | 1 | 89 | 6 | 23 | 44 | 27 |
| 3 | 1.5 | 1.5 | 1 | 80 | 12.1 | 37.2 | 37.5 | 13.2 |

[1]triphenylphosphine oxide.
[2]diphenyl(4-methoxyphenyl)phosphine oxide
[3]bis(4-methoxyphenyl)phenylphosphine oxide
[4]tris(4-methoxyphenyl)phosphine oxide.

2c. Bis(4-methoxyphenyl)(4-methylphenyl)phosphine Oxide Mixture.

Magnesium (1430 g, 58.8 mol), tetrahydrofuran (12 L), and 1,2-dibromoethane (2.2 g, 0.012 mol) were stirred under nitrogen for 1 h. The mixture was then heated to reflux and the heating stopped. A mixture of 4-bromotoluene (3268 g, 19.1 mol) and 4-bromoanisole (7150 g, 38.2 mol) was added at a rate to maintain a slow reflux (67° C.) over a period of 4 h. The reaction mixture was then held for a further 5 h at 70° C. Phosphorus oxychloride (2930 g, 19.1 mol) was added at a rate to maintain a temperature of 70° C. (5 h). The reaction was then held at 70° C. for a further 5 h. The reaction mixture was then worked up to give the product mixture (5563.8 g, 83%) as an amber colored oil upon concentration. $^{31}$P NMR: ($d_6$-DMSO) δ 27.3 (s), 27.1 (s), 26.9 (s), 26.9 (s), 26.7 (s). GC(area %): tris(4-methylphenyl) phosphine oxide 3.8%, bis(4-methylphenyl)(4-methoxyphenyl)phosphine oxide 21.0%, bis(4-methoxyphenyl)(4-methylphenyl)phosphine oxide 39.4%, and tris(4-methoxyphenyl)phosphine oxide 25.1%.

2d. Bis(4-hydroxyphenyl)(4-methylphenyl)phosphine Oxide Mixture.

A mixture of bis(4-methoxyphenyl)(4-methylphenyl)phosphine oxide mixture (470.2 g, 1.33 mol), hydrobromic acid (1458.1 g, 48%, 8.65 mol), and potassium bromide (45.0 g, 0.378 mol) were stirred for 112 h at 110° C. The flask was fitted with a sodium sulfite scrubber for containment of methyl bromide. The lower aqueous layer was removed and the molten product layer was worked up to give bis(4-hydroxyphenyl)-(4-methylphenyl)phosphine oxide mixture as a tan powder (292.8 g, 77% yield). m.p. (DSC): 142.5° C. $^{31}$P NMR ($d_6$-DMSO): 28.33 (s, 90.1%), 28.14 (s, 9.86%). LC(area %, THF:MeCN:water, 5:15:30): 16.2, 48.9, 20.1.

2e. Bis(4-methoxyphenyl)-2,4,5-trimethylphenylphosphine oxide mixture.

A reaction flask under nitrogen containing magnesium turnings (120 g, 4.94 mol) and 412 mL THF was charged with 0.5 g of 1,2-dibromoethane and heated to reflux for 1 h. A separate flask was charged with 5-bromo-1,2,4- trimethylbenzene (300 g, 1.51 mol), dissolved in 568 mL of THF. The heat was removed from the first flask and the 5-bromo-1,2,4-trimethylbenzene solution was added dropwise at a rate to maintain reflux. 4-Bromoanisole (536.7 g, 3.01 mol) was then added over 1.5 h at 75° C. reaction temperature. After holding the reaction mixture overnight, POCl$_3$ (231 g, 1.51 mol) was added dropwise at 40–80° C. The product mixture was isolated by aqueous workup to give 453.6 g (79% yield) of product mixture as a viscous liquid. The structure was consistent with NMR data.

2f. Bis(4-hydroxyphenyl)-2,4,5-trimethylphenylphosphine Oxide Mixture.

A reaction flask containing the bis(4-methoxyphenyl)-2,4,5-trimethylphenylphosphine. oxide mixture (443.7 g) was charged with 48% aq. HBr (934 mL) and KBr (59.5 g). The flask was fitted with a sodium sulfite scrubber for containment of methyl bromide. The reaction mixture was heated to reflux (118° C.) and maintained at reflux until complete based on HPLC analysis. The molten product was worked up to give 283.3 g of bis(4-hydroxyphenyl)-2,4,5-trimethylphenylphosphine oxide mixture as a cream solid (68.9% yield). The ratio of products in the mixture based on $^{31}$P NMR was 39% tris(4-hydroxyphenyl)phosphine oxide, 49% bis(4-hydroxyphenyl)-2,4,5-trimethylphenylphosphine oxide, 11% di-2,4,5-trimethylphenyl-4-hydroxyphenylphosphine oxide, and 1% tris(2,4,5-triethylphenyl)phosphine oxide.

2g. Bis(4-methoxyphenyl)(1-naphthyl)phosphine Oxide Mixture.

A mixture of magnesium (125.2 g, 5.15 mol), 1,2-dibromoethane (0.1 g, 0.5 mmol) and dry THF (1 L) were stirred under a blanket of nitrogen at rt for 1 h. The mixture was brought to 65° C. and 1-bromonaphthalene (343.7 g, 1.66 mol) was added by drop. Once the reaction initiated, the heating was removed and the 1-bromonaphthalene addition was continued for 2 h at a rate to maintain 55° C. 4-Bromoanisole (623.5 g, 3.33 mol) was then added over 4 h. The temperature was adjusted to 65° C. and held for a further 3 h. Phosphorus oxychloride (255.5 g, 1.66 mol) was then added by drop to maintain a temperature of 50–60° C. over 6 hours. The temperature was then adjusted to 50° C. and held overnight. The reaction mixture worked up to afford bis(4-methoxyphenyl)(1-naphthyl)phosphine oxide mixture as an amber solid (508 g, 79 yield %). $^{31}$P NMR (CDCl$_3$): δ 37.49 (s, 3.0%), 35.32 (s, 2.4%), 33.64 (s, 31.1%), 30.37 (s, 50.8%), 19.59 (s, 12.7%).

2h. Bis(4-hydroxyphenyl)(1-naphthyl)phosphine Oxide Mixture.

Bis(4-methoxyphenyl)(1-naphthyl)phosphine oxide (352 g, 0.906 mol), hydrobromic acid (1474 g, 48%, 8.74 mol), and potassium bromide (45 g, 0.378 mol) were heated at 110° C. for 96 h. The flask was fitted with a sodium sulfite scrubber for containment of methyl bromide. The mixture was worked up to give the product as a brown solid (267 g, 82% yield). $^{31}$P NMR (d$_6$-DMSO): δ 35.19 (s, 5.2%), 30.96 (s, 74.4%), 27.16 (s, 19.3%). m.p. (DSC): 114.7° C.

2i. Bis(4-methoxyphenyl)-tert-butylphosphine Oxide Mixture.

Magnesium (30.1 g, 1.24 mol), tetrahydrofuran (400 mL), and 1,2-dibromoethane (1 drop) were stirred under nitrogen for 1 h. The mixture was then heated to reflux and the heating stopped. 4-Bromoanisole (224.4 g, 1.20 mol) was added as a mixture at a rate to maintain a slow reflux (67° C.) over a period of 4 h. The reaction mixture was then held for a further 3 h at 70° C. To a tetrahydrofuran (500 mL) solution of phosphorus oxychloride (92.0 g, 0.60 mol) was added by drop tert-butylmagnesium chloride (300 mL, 2.0 M, 0.60 mole) over 5.5 h and held at 40° C. for 1 h. Then the 4-methoxyphenylmagnesium bromide solution prepared above was added by drop over 2 h at a rate to maintain 40° C. The mixture was allowed to stir for 2 days at rt. The reaction mixture was worked up to yield a pale-yellow sticky solid (135.6 g, 71%). $^{31}$P NMR (d$_6$-DMSO): δ 44.7 (s, 43.0%), 37.8 (s, 7.0%), 26.5 (s, 7.6%), 25.4 (s, 36.4%), 14.9 (s, 6.0%).

2j. Bis(4-hydroxyphenyl)-tert-butylphosphine oxide mixture.

Bis(4-methoxyphenyl)-tert-butylphosphine oxide mixture (25.0 g), hydrobromic acid (770 g, 48%), and potassium bromide (30.0 g) were stirred for 25 h at 120° C. The flask was fitted with a sodium sulfite scrubber for containment of methyl bromide. The reaction mixture was worked up to give a tan solid (9.6 g, 40%). $^{31}$P NMR (d$_6$-DMSO): δ 46.3 (s, 31.8%), 39.6 (s, 31.7%), 28.7 (s, 20.4%), −8.2 (s, 16.1%).

Example 3

Forwarding Reactions Using Hydroxyarylphosphine Oxides

3a. Bis(4-hydroxyphenyl)phenylphosphine oxide mixture/EPON 828 Adduct.

Bis(4-hydroxyphenyl)phenylphosphine oxide mixture (BHPPPOM) (329 g) and EPON 828 (1318 g) were heated at 170° C. for 40 min. 1-Methoxy-2-propanol (410 g) was then added to afford an amber colored resin. Solution EEW: 460.9. % Solids: 86.

This procedure was repeated with different reactant stoichiometries to affect the final oligomer molecular weight and phosphorus content as shown in Table 2.

TABLE 2

Forwarding Reaction of EPON 828 with Bis(hydroxyphenyl)phenylphosphine oxide Mixture (BHPPPOM).

| BHPPPOM | EPON 828 | PGME | % Solids | EEW | Calc. % P[a] | Calc. MW[b] |
|---|---|---|---|---|---|---|
| 80.4 g | 616.6 g | 174 g | 80.0 | 257.9 | 1 | 412.6 |
| 329 g | 1218 g | 410 g | 86.0 | 460.9 | 2 | 792.8 |
| 210.0 g | 452.4 g | 166 g | 84.0 | 891.0 | 3 | 1496 |

[a]Calc. from % P content of BHPPOM.
[b]Calc. from EEW.

3b. Bis(4-hydroxyphenyl)(4-methylphenyl)phosphine Oxide Mixture/EPON 828 Adduct.

Bis(4-hydroxyphenyl)(4-methylphenyl)phosphine oxide mixture (100 g) and EPON 828 (350 g) were heated at 170° C. for 90 min. 1-Methoxy-2-propanol (PGME) (112 g) was then added to afford an amber colored resin. Solution EEW: 463.2. % Solids: 81.

3c. Bis(4-hydroxyphenyl)phenylphosphine Oxide/EPON 828 Adduct.

Bis(4-hydroxyphenyl)phenylphosphine oxide (196.0 g) and EPON 828 (782.0 g) were heated at 170° C. for 40 min. The clear dark brown resin was then diluted with 218 g of PGME and filtered hot through a pad of glass wool. Solution EEW: 454; % Solids: 88.7.

3d. Bis(4-hydroxyphenyl)phenylphosphine Oxide Mixture Enriched in Tris(4-hydroxyphenyl)phosphine Oxide/EPON 828 Adduct.

A mixture of EPON 828 (330.9 g) and a sample of the bis(4-hydroxyphenyl)phenylphosphine oxide mixture assaying to contain triphenylphosphine oxide (3.0 g), diphenyl (4-hydroxyphenyl)phosphine oxide (13.7 g), bis(4-hydroxyphenyl)phenylphosphine oxide (30.7 g) and tris(4-hydroxyphenyl)phosphine oxide (49.2 g) were heated at 170° C. for 40 min. PGME (140 g) was then added to give a brown resin. Solution EEW: 521. % Solids: 88.

3e. Bis(4-Hydroxyphenyl)phenylphosphine Oxide Mixture Enriched in Diphenyl(4-hydroxyphenyl)phosphine Oxide/EPON 828 Adduct.

A mixture of EPON 828 (352.9 g), bis(4-hydroxyphenyl)phenylphosphine oxide mixture assaying to contain triphenylphosphine oxide (3.0 g), diphenyl(4-hydroxyphenyl) phosphine oxide (39.2 g), bis(4-hydroxyphenyl)phenylphosphine oxide (30.7 g) and tris(4-hydroxyphenyl) phosphine oxide (19.2 g) was heated at 170° C. for 40 min. PGME (111 g) was then added to give a brown resin. Solution EEW: 396. % Solids: 83.8.

3f. Tris(4-hydroxyphenyl)phosphine Oxide/EPON 828 Adduct.

A mixture of tris(4-hydroxyphenyl)phosphine oxide (prepared in a method analogous to example 2a,b using three equivalents of bromoanisole) (21.2 g) with EPON 828 (79.3 g) was heated over a 7 min period to 150° C. The mixture to this point was a slurry of the phosphine oxide in EPON 828. In the next 4 min., the pot reached a temperature of 180° C., and this point a portion of the phosphine oxide aggregated into a polymeric mass.

Following the procedures as set out in Example 3a, various epoxy resins of this invention are prepared employing the pure hydroxyarylphosphine oxides as prepared in accordance with Example 1 or the dihydroxyarylphosphine oxide mixtures as prepared in accordance with Example 2 and utilizing various epoxy resins known in the art. A representative list of hydroxyarylphosphine oxides and the epoxy resins that can be employed are summarized below:

| Hydroxyarylphosphine oxides | Epoxy Resins |
| --- | --- |
| Bis(4-hydroxyphenyl)phenylphosphine Oxide | EPON 828 |
| Tris(4-hydroxyphenyl)phosphine oxide | D.E.N. ™ |
| Bis(4-hydroxyphenyl)(2-naphthyl)phosphine Oxide | Quatrex ™ |
| Bis(4-hydroxyphenyl)(1-naphthyl)phosphine Oxide | Phenol novolaks |
| Bis(4-hydroxyphenyl)(4-methylphenyl)phosphine Oxide | Glycidyl ether of bisphenol-F |
| Bis(4-hydroxyphenyl)(2,4,5-trimethylphenyl)phosphine Oxide | Epoxy phenol novolak resins |
| Bis(4-hydroxyphenyl)-tert-butylphenylphosphine Oxide | Epoxy cresol novolak resins |
| Bis(4-hydroxyphenyl)phenylphosphine Oxide Mixture | |
| Bis(4-hydroxyphenyl)(4-methylphenyl)phosphine Oxide Mixture | |
| Bis(4-hydroxyphenyl)-2,4,5-trimethylphenylphosphine Oxide Mixture | |
| Bis(4-hydroxyphenyl)(1-naphthyl)phosphine Oxide Mixture | |
| Bis(4-hydroxyphenyl)-tert-butylphosphine Oxide Mixture | |

Example 4

Glycidyl Ether Derivatives

4a. Bis(4-glycidoxyphenyl)phenylphosphine Oxide Mixture.

Bis(4-hydroxyphenyl)phenylphosphine oxide mixture (962.0 g, 3.10 mol), epichlorohydrin (2052.0 g, 22.18 mol), and methyl cellosolve (100 g) were heated to 80° C. Solid sodium hydroxide (260.4 g, 6.51) was added slowly over 1.5 h.

Towards the end of the addition, the exothermic reaction was cooled in an ice-bath. The volatiles were then stripped under vacuum to a temperature of 160° C. Then methylene chloride (3 L) was added and the sodium chloride was removed by filtration. After filtration, the volatiles were removed under vacuum at 150° C., and PGME (258 g) was added to give an amber resin. Solution EEW: 407.0. % Solids: 88.

4b. Tris(2-glycidoxyphenyl)phosphine Oxide.

Heat a mixture of tris(2-hydroxyphenyl)phosphine oxide (198.2 g, 0.607 mol), epichlorohydrin (674.0 g, 7.28 mol), and methyl cellosolve (75 g) to 80° C. Add solid sodium hydroxide (76.4 g, 1.91) slowly over 1.5 h. Moderate the reaction exotherm by cooling the reaction mixture in an ice-bath. Remove the volatiles under vacuum at a temperature of 160° C. Then add methylene chloride (3 L) and remove sodium chloride by filtration. After filtration, remove the volatiles under vacuum at 150° C. and isolate the title compound.

Following the procedures as set out in Example 4a various glycidoxyaryl phosphine oxides and mixtures are prepared employing the pure hydroxyarylphosphine oxides as prepared in accordance with Example 1 or the dihydroxyarylphosphine oxide mixtures as prepared in accordance with Example 2, the glycidyl ethers thus prepared are summarized below:

Bis(4-glycidoxyphenyl)phenylphosphine Oxide
Tris(4-glycidoxyphenyl)phosphine Oxide
Bis(4-glycidoxyphenyl)(2-naphthyl)phosphine Oxide
Bis(4-glycidoxyphenyl)(1-naphthyl)phosphine Oxide
Bis(4-glycidoxyphenyl)(4-methylphenyl)phosphine Oxide
Bis(4-glycidoxyphenyl)(2,4,5-trimethylphenyl)phosphine Oxide
Bis(4-glycidoxyphenyl)-tert-butylphenylphosphine Oxide
Bis(4-glycidoxyphenyl)phenylphosphine Oxide Mixture
Bis(4-glycidoxyphenyl)(4-methylphenyl)phosphine Oxide Mixture
Bis(4-glycidoxyphenyl)-2,4,5-trimethylphenylphosphine Oxide Mixture
Bis(4-glycidoxyphenyl)(1-naphthyl)phosphine Oxide Mixture
Bis(4-glycidoxyphenyl)(2-naphthyl)phosphine Oxide Mixture
Bis(4-glycidoxyphenyl)-tert-butylphosphine Oxide Mixture Example 5

Glycidyl Ether Derivative and Forwarding Bis(4-glycidoxyphenyl)phenylphosphine Oxide Mixture/Bis(4-hydroxyphenyl)phenylphosphine Oxide Mixture Adduct.

Bis(4-hydroxyphenyl)phenylphosphine oxide mixture (120 g, 0.387 mol), epichlorohydrin (256 g, 2.77 mol), and methyl cellosolve (13 g) were heated to 80° C. Solid sodium hydroxide (32.6 g, 0.815 mol) was added slowly over an hour and a half. Towards the end of the addition, the reaction exothermed and had to be cooled in an ice-bath. Then 500 mL of methylene chloride was added and the sodium chloride was removed by filtration. The organics were stripped under vacuum to 150° C. Bis(4-hydroxyphenyl) phenylphosphine oxide (25.8 g, 0.0831 mol) was then added and held at 180° C. for 30 min. The resin was then diluted with 56 g of PGME. Solution EEW: 610. % Solids: 83.

Following the procedures as set out in Example 5 various glycidoxyaryl phosphine oxides and mixtures are prepared employing the pure hydroxyarylphosphine oxides as prepared in accordance with Example 1 or the dihydroxyarylphosphine oxide mixtures as prepared in accordance with Example 2, the glycidyl ethers thus prepared are treated with one or more of the pure hydroxyarylphosphine oxides of Example 1 or the dihydroxyarylphosphine oxide mixtures of Example 2 to form various epoxy resins of this invention.

Example 6

Epoxy Laminate

To a 32 oz glass jar 211 g (100 phr) of epoxy resin solids, prepared as described in Example 3a, 5.67 g (2.7 phr) dicyandiamide, 0.1 g 2-methylimidazole (0.05 phr), and 35 g dimethylformamide (17 phr) was added and stirred vigorously for 15 min and then allowed to sit at 25° C. for 24 hours. Several plies of glass cloth (12 in$^2$, 7628 style) were individually coated with the above varnish. The impregnated sheets were then held into a laboratory oven at a temperature of 170° C. for 3 minutes to form the prepregs. Then eight of the prepreg plies were stacked together with two sheets of copper foil on either side and pressed together in a hydraulic press for 1.2 hours at 205° C. to produce a consolidated laminate.

Following the procedures of Example 6 and employing the various other epoxy resins of Examples 3, 4 or 5, various other epoxy laminates of this invention are prepared.

Example 7

Epoxy Laminate Comparisons

This Example 7 demonstrates the flame-retardant activity of various phosphine oxide mixtures of the present invention. In this Example 7, a series of laminates was prepared using a few of the preferred embodiments of the invention as described hereinabove. The epoxy laminates were prepared following the procedures as set forth in Example 6. The laminates so formed were tested for their $T_g$, for thermal properties according to TGA, for combustibility according to UL 94, and time taken to delaminate at 260° C. according to the T-260 test. Table 3 summarizes these thermomechanical properties of various laminates formed in accordance with the procedures of Example 6 and employing the phosphine oxides formed in accordance with Examples 3a, 3c, 3d and 3e.

TABLE 3

Comparison of Bis(4-hydroxyphenyl)phenylphosphine Oxide Mixture/EPON 828 Adduct Using Different Ratios of Mixture Components.

| Patent Example Resin | Components[a] (phr) | % P | Tg (TMA) | TGA (5% loss) | UL 94[b] $T_1$, $t_2$ (sec) | T-260[c] (minutes) |
|---|---|---|---|---|---|---|
| 3a (mixture) | Resin 100 DICY 2.7 2MI 0.05 | 1.8 | 146 | 372 | 55, 0 | >18 |
| 3c (pure bis) | Resin 100 DICY 2.8 2MI 0.05 | 1.9 | 143 | 374 | 75, 0 | >19 |
| 3d (high tris) | Resin 100 DICY 2.4 2MI 0.035 | 1.9 | 144 | 372 | 34, 0 | >19 |
| 3e (high mono) | Resin 100 DICY 3.2 2MI 0.9 | 1.9 | 137 | 369 | 52, 0 | >19 |

[a]The solvents N,N-dimethylformamide and Dowanol PM (1-methoxy-2-propanol) were used to dissolve the materials and the hardeners were used at the levels indicated (see Example 7).
[b]Samples 3a, 3d, and 3e gave self-extinguishing flames with only approximately one-third of the coupon being consumed at the edges only. Sample 3c burned to the clamp at the edges only.
[c]The test was stopped at the time indicated.

According to prior art (JP 186186A), the pure bis(4-hydroxyphenlyl)phenylphosphine oxide displayed flame retardant properties when used with a novolak epoxy resin system, giving a V-0 in the UL-94 test. The Table 3 data in this study compares the relative flame retardant activity of the corresponding mixture material with the pure bis compound using a simple formulation based on the bisphenol A diglycidyl ether, which is known to be more difficult to flame-retard. Noteworthy observations are that higher levels of the trishydroxy did not impact the Tg, but a higher level of monohydroxy does. The mixtures demonstrated improved inherent flame retardant properties vs. the pure bis material, as evidenced by the self-extinguishing nature in the UL-94 test and the relative burn times. The mixture is comparable to the pure bis with regards to the Tg. High thermal stability is apparent as evidenced by the high values obtained in the TGA and T-260 analyses.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A flame retardant epoxy composition derived from a mixture of hydroxyarylphosphine oxides by way of reacting said mixture of hydroxyarylphosphine oxides with an epoxy resin composition, said mixture of hydroxyarylphosphine oxides comprising:

(a) a mono(hydroxyaryl)phosphine oxide of the formula:

(I)

wherein $R_1$ is a divalent, substituted or unsubstituted arylene moiety and $R_2$ is a monovalent, substituted or unsubstituted aryl moiety or is an alkyl moiety or is an aralkyl moiety; and (b) a bis(hydroxyaryl)phosphine oxide of the formula:

(II)

wherein $R_1$, $R_2$ are defined as above; and (c) a tris(hydroxyaryl)phosphine oxide of the formula:

(III)

wherein $R_1$, is defined as above; and (d) optionally containing minor amounts of a pentavalent phosphine oxide of the formula:

(IV)

wherein $R_2$ is defined as above.

2. A resin-impregnated composite comprising a reinforcing component and the flame retardant epoxy composition according to claim 1, at least partially cured.

3. The resin-impregnated composite according to claim 2, including a glass filler, a glass fiber or a glass fabric.

4. The resin-impregnated composite according to claim 3, wherein said composite includes a glass fabric.

5. A flame retardant curable composition comprising at least one component selected from the group consisting of:
(i) an epoxy component derived from a mixture of hydroxyarylphosphine oxides by way of reacting said mixture of hydroxyarylphosphine oxides with a diglycidyl ether or mixture of diglycidyl ethers or polyglycidyl ethers; and
(ii) a mixture of glycidyl ethers derived from said mixture of hydroxyarylphosphine oxides, said mixture of hydroxyarylphosphine oxides comprising:

(a) a mono(hydroxyaryl)phosphine oxide of the formula:

(I)

wherein $R_1$ is a divalent, substituted or unsubstituted arylene moiety and $R_2$ is a monovalent, substituted or unsubstituted aryl moiety or is an alkyl moiety or is an aralkyl moiety; and (b) a bis(hydroxyaryl)phosphine oxide of the formula:

(II)

wherein $R_1$ and $R_2$ are defined as above; and (c) a tris(hydroxyaryl)phosphine oxide of the formula:

(III)

wherein $R_1$ is defined as above; and (d) optionally containing minor amounts of a pentavalent phosphine oxide of the formula:

(IV)

wherein $R_2$ is defined as above.

6. The curable composition according to claim 5, further comprising an epoxy resin based on epichlorohydrin and bisphenol A, bisphenol F, or a novolak epoxy resin.

7. The curable composition according to claim 5, wherein at least one component is an oligomer derived from the reaction of said mixture of hydroxyarylphosphine oxides with a mixture of glycidyl ethers derived from said mixture of hydroxyarylphosphine oxides.

8. A resin-impregnated composite comprising a reinforcing component and the flame retardant curable composition according to claim 5, at least partially cured.

9. The resin-impregnated composite according to claim 8, including a glass filler, a glass fiber or a glass fabric.

10. The resin-impregnated composite according to claim 9, wherein said composite includes a glass fabric.

* * * * *